(12) United States Patent
Lonergan (10) Patent No.: US 6,455,873 B1
(45) Date of Patent: Sep. 24, 2002

(54) DEVICES HAVING A SEMICONDUCTOR/ CONDUCTING POLYMER INTERFACE

(75) Inventor: Mark C. Lonergan, Eugene, OR (US)

(73) Assignee: State of Oregon Acting by and through the State Board of Higher Education on behalf of the University of Oregon, Eugene, OR (US)

( * ) Notice: Subject to any disclaimer, the term of this patent is extended or adjusted under 35 U.S.C. 154(b) by 0 days.

(21) Appl. No.: 09/204,621

(22) Filed: Dec. 1, 1998

Related U.S. Application Data (60) Provisional application No. 60/067,798, filed on Dec. 3, 1997.

(51) Int. Cl.⁷ .................... H01L 35/24; C08F 8/00; B05D 5/12; G01N 27/00
(52) U.S. Cl. .................... 257/40; 257/88; 257/99; 257/103; 257/461; 257/431; 257/448
(58) Field of Search .................... 257/787, 40, 431, 257/436, 448, 464, 184, 440, 461, 99, 88, 91, 103

(56) References Cited

U.S. PATENT DOCUMENTS

| | | | | |
|---|---|---|---|---|
| 4,895,705 A | * | 1/1990 | Wrighton et al. | 422/68 |
| 4,900,135 A | * | 2/1990 | Yuasa et al. | 350/354 |
| 4,936,956 A | * | 6/1990 | Wrighton | 204/403 |
| 5,034,192 A | * | 7/1991 | Wrighton et al. | 422/82.02 |
| 5,292,792 A | * | 3/1994 | Carew | 524/550 |
| 5,407,699 A | * | 4/1995 | Myers | 427/121 |
| 5,444,330 A | * | 8/1995 | Leventis et al. | 313/506 |
| 5,677,546 A | * | 10/1997 | Yu | 257/40 |
| 5,910,854 A | * | 6/1999 | Varaprasad et al. | 359/273 |
| 5,965,281 A | * | 10/1999 | Cao | 257/40 |
| 6,060,327 A | * | 5/2000 | Keen | 436/518 |
| 6,198,091 B1 | * | 3/2001 | Forrest et al. | 257/40 |

OTHER PUBLICATIONS

Sailor, Michael J., et al., "Electronic Properties of Junctions Between Silicon and Organic Conducting Polymers," *Nature*, vol. 346, 155–157 (Jul. 12, 1990).

Karp Christoph D., "Photoelectrochemistry of Si/Polymer and Si/Metal/Solution Interfaces," Thesis submitted Nov. 16, 1994, Division of Chemistry and Chemical Engineering, California Institute of Technology, Pasadena, California.

* cited by examiner

Primary Examiner—Alexander O. Williams
(74) Attorney, Agent, or Firm—Klarquist Sparkman, LLP (57) ABSTRACT

Microelectronic devices have a semiconductor/conducting polymer interface are disclosed. The conducting polymer may be electrically contacted in a manner to assure that it remains exposed to the environment. If the environment is an inert electrolyte to which additional electrodes are contacted, the conducting polymer can be electrochemically oxidized or reduced to control its electrochemical potential and a tunable (variable barrier) diode results. This tunable diode is a device that rectifies current like a traditional diode, but unlike traditional diodes, the effective barrier height of the tunable diode can be actively controlled. This control can be an element of an active device or a means for fabricating fixed barrier diodes with controlled barrier heights. Alternatively, the environment can contain an analyte to be sensed, either directly or through a mediating layer. The electrical characteristics (e.g. current-voltage or capacitance voltage) of the semiconductor/conducting polymer interface can be used to sense the analyte if it induces a change in the electrochemical potential of the conducting polymer.

11 Claims, 6 Drawing Sheets

DEVICES HAVING A SEMICONDUCTOR/CONDUCTING POLYMER INTERFACE

This application claims the benefit of U.S. provisional application No. 60/067,798, filed Dec. 3, 1997.

BACKGROUND AND SUMMARY OF THE INVENTION

The present invention relates to microelectronic devices and sensors that have a semiconductor/conducting polymer interface.

The operation of traditional semiconductor devices such as diodes and transistors relies on interfacial properties. Such devices are generally based on interfaces or multilayer structures consisting of conducting (e.g. metals such as Au or Ni), semiconducting (e.g. Si, GaAs) and insulating materials (e.g. SiO$_2$) (S. M. Sze, *Physics of Semiconductor Devices*, Wiley, New York (1981)). Conducting polymers have been introduced into a number of these devices by simple substitution (see e.g. J. H. Burroughs, C. A. Jones, and R. H. Friend, *Nature* 335, 137 (1988); J. H. Burrough et al., *Nature* 347, 539 (1990)). The conducting polymer serves as a replacement for a metal or a semiconductor in traditional device architectures. Although the introduction of a conducting polymer may bring certain advantages in processing and/or chemical diversity, the operational principle of the vast majority of these conducting polymer devices is identical to their more traditional analogues.

There is one notable exception to the simple substitutional approach that has dominated the design of conducting polymer devices. A broad class of devices has been developed whose operation relies on the ability to modulate the conductivity of a conducting polymer through manipulation of its electrochemical potential. This property has served as the basis for electrochemical transistors (see e.g. J. W. Thackeray, H. S. White, M. S. Wrighton *J. Phys. Chem.* 89, 5133 (1985); E. P. Lofton, J. W. Thackeray, and M. S. Wrighton, *J. Phys. Chem.* 90, 6080 (1986)) and a wide range of conductometric sensors (see e.g. Pearce et al., *Analyst* 118, 371–377 (1993), Shurmer et al. Sens. Act. B 4, 29–33 (1991), Y. Miwa et al., *Bull. Chem. Soc. Jpn.* 67, 2864–6 (1994); A. Talaie, *Polymer* 38, 1145–1150 (1997); P. N. Bartlett et al. *Anal. Chem.* 70, 3685–3694 (1998)). Unlike traditional semiconductor devices that rely on the electrical characteristics of interfaces, these devices rely on changes in the bulk electrical characteristics of conjugated polymers. In the case of electrochemical transistors, a "gate" potential is used to control the electrochemical potential of a conducting polymer that is one electrode of an electrochemical cell. A minimum of two electrodes, termed source and drain, contacted to the polymer serve to sense the change in conductivity observed in response to the gate potential. Since the gate potential serves to modulate the current flowing (induced by a constant source-drain potential) across the source and drain electrodes, amplification and logic functions become possible. In the case of sensors, the gate is the environment. If an analyte in the gating environment induces a change in the electrochemical potential of the conducting polymer, its presence will be sensed through a change in conductivity.

This disclosure generally concerns itself with hybrid conducting polymer devices that rely on the electrical properties of semiconductor/conducting polymer interfaces and their response to changes in the bulk electrical characteristics of the conducting polymer. The electrical characteristics of the conducting polymer are either actively controlled using external electronics or controlled by analytes in an environment to which it is contacted, either directly or through a mediating layer. In the case of active electrochemical control, a variable barrier or tunable diode results. In the case of control by analytes in an environment, a general electrochemical transducer for sensing applications results. A method of generating semiconductor diodes with specific electrical characteristics is also disclosed.

For the purpose of this disclosure, a semiconductor diode is defined as an interface between a material that conducts electricity and that can support an electric field through the formation of a depletion region (typically but not limited to an inorganic semiconductor such as Si, GaAs or InP) and another electrical conductor (such as but not limited to a metal or conducting polymer). In general, the current-voltage characteristics of such a semiconductor diode are described by the following equation relating current, $I_{PS}$, to applied potential, $V_{PS}$:

$$I_{ps} = I_o\left[1 - \exp\left(-\frac{qV_{ps}}{nkT}\right)\right] \quad (1)$$

where $I_0$ is the equilibrium exchange current or reverse saturation current, n is the diode quality factor, k is the Boltzmann constant, q is the elementary charge, and T is the temperature. The ps subscripts indicate reference to a conducting polymer/semiconductor interface. Both $I_o$ and n depend on the details of current flow at the interface with the theoretical minimum of n=1 generally considered ideal. $I_o$ is given by a number of parameters as described by the following equation, with some loss of generality, for an n-type inorganic semiconductor where majority carrier transfer dominates current flow:

$$I_o = aqk_n N_C \exp\left[\frac{-q\phi_b}{kT}\right] \quad (2)$$

where a is the active device area, $k_n$ is the surface recombination velocity, and $N_c$ is the effective density of states at the conduction band edge of the n-type inorganic semiconductor, and $\phi_b$ is the Schottky barrier height. It is noted that the barrier height is at times considered as an effective empirical parameter, but its strict definition relates to the magnitude of the interfacial potential barrier. Herein, we used the barrier height in the empirical sense although at times this is equivalent to the stricter definition.

The Schottky barrier height, $\phi_b$, is a central parameter determining the precise electrical characteristics of a diode where majority carrier transfer dominates current flow. Through choice of materials, it is possible to exert control over the barrier height of a diode. However, for many semiconductors, in particular so-called small band gap semiconductors, only a very small level of control is possible (E. H. Rhoderick and R. H. Williams, Metal-Semiconductor Contacts, P. Hammond and G. L. Grimsdale, Eds. (Monographs in Electrical and Electronic Engineering, Oxford Univ. Press, Oxford, ed. 2, (1988), vol. 19). For instance, a series of semiconductor diodes fabricated from clean n-type indium phosphide (n-InP) and the following metals—Ag, Cr, Cu, Au, Pd, Mn, Sn, Al, and N—allows the effective barrier height to be controlled over a range of only 0.2 eV (N. Newman et al., *Appl. Phys. Lett.* 46, 1176 (1985)). The tunable diode disclosed herein allows for extensive control over the effective barrier height of semiconductor interfaces. Furthermore, this control is continuous and, if desired, available in a single tunable device rather than in a series of separate devices. For comparison, an embodiment of the tunable diode based on n-InP allows for the effective barrier to be controlled by more than twice that possible with the series of metals described above and again in a single device if so desired.

Certain disclosed devices can serve as general electrochemical transducers. Such transducers can be interfaced to nearly any sensing scheme that relies on potentiometric detection. Classic potentiometric detection schemes measure the electrochemical potential of a material or the junction potential of an interface by comparing the potential signal at one electrode with a second reference electrode such as a saturated calomel electrode (SCE) (A. J. Bard and L. R. Faulkner, *Electrochemical Methods* (Wiley, New York, 1980)) Several alternatives to this classic mode of measuring electrochemical potential based on conducting polymers have been developed and have served as the basis for the development of a wide range of sensors for analytes such as, protons, glucose, and organic vapors (see e.g. Pearce et al., *Analyst* 118, 371–377 (1993), Shurmer et al. Sens. Act. B 4, 29–33 (1991), Y. Miwa et al., *Bull. Chem. Soc. Jpn.* 67, 2864–6 (1994); A. Talaie, *Polymer* 38, 1145–1150 (1997); P. N. Bartlett et al. *Anal. Chem.* 70, 3685–3694 (1998), L. Martin et al., *Thin Solid Films* 286, 252–255 (1996), J. Cassidy et al., *Anal. Chem. Symp. Ser.* 25, 309–14 (1986), M. Josowicz and J. Janata, *Anal. Chem.* 58, 514–517 (1986)). These conducting polymer devices rely on detecting changes in the electrochemical potential of a conducting polymer induced by an analyte either directly or indirectly, for instance through an analyte specific membrane or with the aid of a redox enzyme. In one scheme, electrochemical potential is sensed by measuring the conductivity of the conducting polymer, a bulk measure which is sensitive to electrochemical potential. There is no need for a reference electrode in this potentiometric detection scheme. In a second scheme, the conducting polymer is used as the gate electrode of an inorganic metal oxide semiconductor field effect transistor. The electrochemical potential of the conducting polymer in essence sets the gate potential of the device and thereby controls the current through it. Again, a separate reference electrode is not necessarily required. This latter scheme is a general one that has been used with a wide range of gate materials, not just conducting polymers.

This disclosure describes a scheme for sensing electrochemical potential using a single electrode consisting of a semiconductor/conducting polymer interface. As was the basis for the tunable diode, the current flow across this interface strongly depends on the electrochemical potential of the conjugated polymer. The electrical characteristics of this interface can hence be used as a potentiometric sensor as long as the conducting polymer has a means to equilibrate with the analyte to be sensed. This approach differs substantially from the two sensing schemes described above. Unlike the simple measure of the polymer's conductivity, the present approach measures the electrical characteristics of a semiconductor interface and has the potential to be much more sensitive. Unlike the conducting polymer modified field effect transistor, the present approach relies on measuring current flow across an interface of which the conducting polymer is a constituent. In the modified field effect transistor, current flow across a wholly inorganic system is measured and influenced by a polymeric or polymer modified gate electrode at a distance.

Semiconductor/conducting polymer interfaces have been reported previously (M. Ozaki et al., *Appl. Phys. Lett.* 35, 83 (1979); O. Inganas et al., *Physica Scripta* 25, 863 (1981); O. Inganas et al., *J. Appl. Phys.* 54, 3636 (1983); Y. Renjuan etal., *Synth. Metals* 41–43, 731 (1991); Turut and F. Koleli, *Physica B*. 192, 279 (1993);. M. J. Sailor et al., *Nature* 346, 155 (1990)). The dependence of the electrical characteristics of semiconductor/conducting polymer interfaces as a function of the electrochemical potential of the conducting polymer has been previously investigated, but for the limited number of interfaces studied thus far, current-voltage properties were found to be largely independent of electrochemical potential of the conducting polymer. Watanabe et al. have measured the electrical properties of press contacted n-Si | poly(pyrrole) interfaces as a function of the electrochemical potential of the poly(pyrrole) (A. Watanabe et al., *Macromolecules* 22, 4231 (1989)). Here, the only effects observed were due to changes in the bulk resistance of the poly (pyrrole) rather 5 than changes in the interfacial properties of the semiconductor/conducting polymer interface. Frank et al. have measured the electrical characteristics of n-CdS | PMeT (PMeT=poly(3-methyl thiophene)) interfaces while exposing the conjugated polymer to aqueous solutions of redox couples of varying electrochemical potentials (A. J. Frank et al., *J. Phys. Chem.* 93, 3818 (1989)). Such a procedure essentially results in the electrochemical potential of the poly(3-methylthiophene) equilibrating to that of the redox electrolyte to which it is contacted. Variation of the electrochemical potential of the redox couple and hence of the electrochemical potential of the conducting polymer did not result in any substantial or systematic change in the electrical properties of the buried n-CdS | PMeT interface. It is believed that these studies failed to reveal any dependence on electrochemical potential due to fabrication techniques (in particular the use of press contacts) in the case of Watanabe et al. and due to material choice (the semiconductor/electrolyte combination selected is subject to deleterious photocorrosion reactions) in the case of Frank et al.

In one of its aspects, the present invention concerns microelectronic devices that have a semiconductor/conducting polymer interface where the conducting polymer is electrically contacted in a manner to assure that it remains exposed to the environment. If the environment is an inert electrolyte to which additional electrodes are contacted, the conducting polymer can be electrochemically oxidized or reduced to control its electrochemical potential and a tunable (variable barrier) diode results. This tunable diode is a device that rectifies current like a traditional diode, but unlike traditional diodes, the effective barrier height of the new device can be actively controlled. This control can be an element of an active device or considered a means for fabricating fixed barrier diodes with controlled barrier heights. Alternatively, the environment can contain an analyte to be sensed, either directly or through a mediating layer. The electrical characteristics (e.g. current-voltage or capacitance voltage) of the semiconductor/conducting polymer interface can be used to sense the analyte if it induces a change in the electrochemical potential of the conducting polymer either directly or through a mediating layer. Here, the semiconductor/conducting polymer interface acts as a general electrochemical transducer. The demonstrated dependence of the electrical characteristics of semiconductor/conducting polymer interfaces on the electrochemical potential of the conducting polymer is thus exploited in new devices.

BRIEF DESCRIPTION OF THE DRAWINGS

In the drawings:

FIGS. 2a and 2b are schematic views of two possible architectures for the tunable diode.

FIG. 4 shows the exponential dependence of current on applied potential. The solid lines are fits to equation (1) with n=1.4.

DETAILED DESCRIPTION

The present invention concerns devices that have a semiconductor/conducting polymer interface. For the purposes of this disclosure, a semiconductor is defined as a conducting material that is capable of supporting an electric field through the formation of a depletion region. Semiconductors include but are not limited to inorganic semiconductors such as silicon, gallium arsenide, indium phosphide, cadmium selenide, cadmium sulfide, titanium dioxide as well as organic semiconductors. The semiconductor may be of various forms including but not limited to single crystalline, polycrystalline, nanocrystalline, and amorphous. Some semiconductor materials may fit within this general definition but not be acceptable, for example very heavily doped semiconductors may not be suitable for use in devices according to the present invention. In such materials it may be difficult to generate sufficiently wide depletion regions to prevent facile tunneling through the interfacial potential barrier. In such a case little dependence of electrical properties on electrochemical potential are expected.

The conducting polymer is defined as a polymeric material or mixture of polymeric materials that can conduct electricity including but not limited to conjugated polymers such as poly(pyrrole)s, poly(thiophene)s, poly(anilines), or poly(acetyelene)s, and redox polymers such as poly(4-vinyl ferrocene) or ruthenium bipyridine coordination complexes with poly(4-vinyl pyridine). Examples of materials that may fit the general definition of a conducting polymer but may not function are polymer-salt complexes such as sodium triflate complexes with poly(propylene) oxide. These are ionic conductors rather than conductors of electrons. Furthermore, these materials may not have well-defined electrochemical potentials that can be varied over a wide range.

The conducting polymer can be electrically contacted in a manner that leaves a usefully large fraction of the conducting polymer exposed to the environment. This can be achieved using a variety of architectures, examples of which are shown in FIGS. 1a–1c.

Figure 1A:
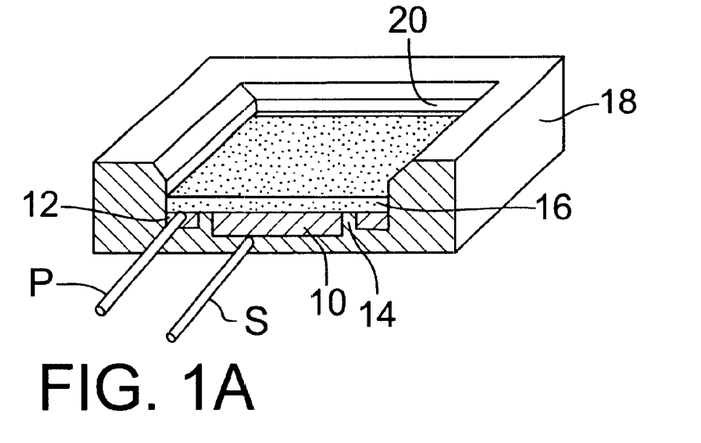
FIGS. 1a–1c are schematic views of three possible architectures for semiconductor/exposed conducting polymer interfaces: (1a) back side contact, (1b) open metallic grid, (1c) porous metallic electrode.

FIG. 1a shows a microelectronic device having a back contact architecture. In this device, a body 10 of semiconductor material lies alongside an electrode or electrical contact 12 that is a body of electrically conductive material such as a metal. The semiconductor material 10 and contact 12 are separated by a body 14 of an insulating material, such as an insulating plastic material. A layer 16 of a conducting polymer overlies and contacts both the body of semiconductor material 10 and contact 12, so that the polymer 16 provides a conductive path between the electrode 12 and the semiconductor material 10. The semiconductor material 10, contact 12, and polymer 16 are encapsulated in a body 18 of the insulating material. Although not required, the body of semiconductor material 10 advantageously is partially encapsulated in the body of insulating material 18 in such a manner that the body of semiconductor material is not exposed to the environment, except through the polymer 16. Conveniently the body 14 and body 18 are formed together as portions of a unitary body of insulating material, which thus serves as a substrate to support both the semiconductor material 10 and contact 12. An opening 20 is provided through the encapsulating material 18 so that the polymer 16 can contact a liquid or solid electrolyte (not shown). Two conductive leads are connected to the device: S is an ohmic contact or lead to the semiconductor material 10, P is an ohmic contact or lead to the electrically conductive contact 12.

Figure 1B:
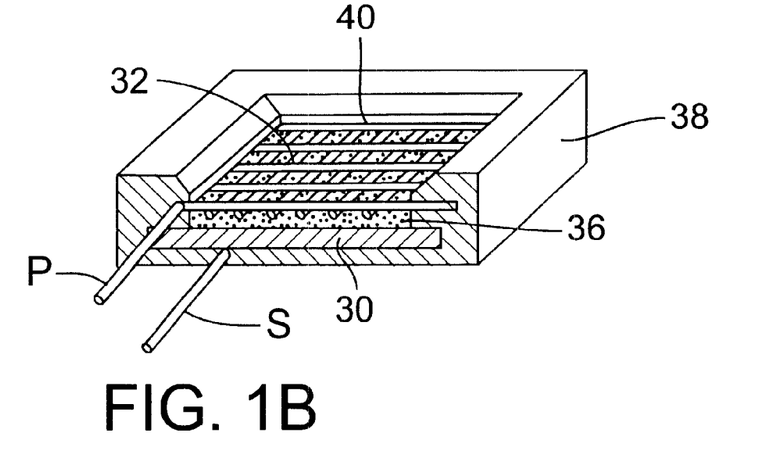

FIG. 1b shows a device having a grid contact architecture. The device has a body 30 of semiconductor material upon which is deposited a layer 36 of a conducting polymer. The polymer is contacted with a metallic grid electrode 32. The semiconductor material 30, electrode 32, and polymer layer 36 are encapsulated in a body 38 of insulating material. An opening 40 is provided through the encapsulating material 38 so that the polymer can contact a liquid or solid electrolyte (not shown) through the electrically conductive grid electrode 32. In this device, S is an ohmic contact to the semiconductor material 30, and P is an ohmic contact to the electrode 32.

Figure 1C:
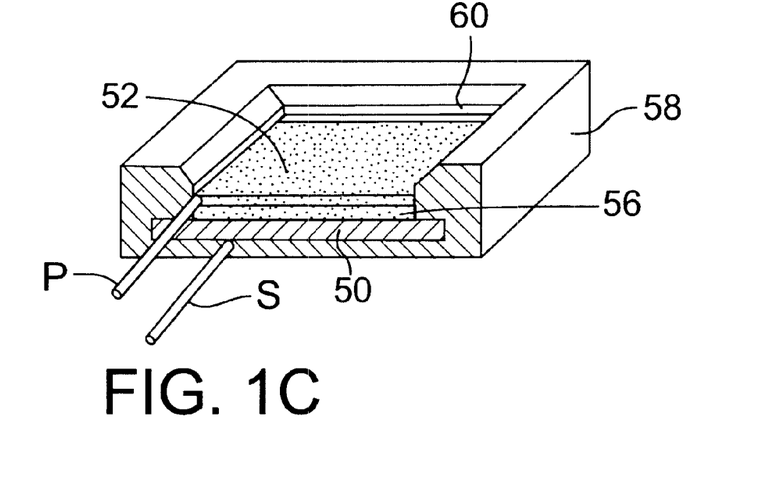

FIG. 1c shows a device having a porous contact architecture. This device has a body 50 of semiconductor material upon which is deposited a layer 56 of a conducting polymer. The exposed surface of the polymer layer 56 is contacted with a porous metallic electrode 52 (see, e.g. P. G. Pickup., J. Amer. Chem. Soc., 106, 1991 (1984)). The semiconductor material 50, electrode 52, and polymer layer 56 are encapsulated in a body 58 of insulating material. An opening 60 is provided through the encapsulating material 58 so that the body of polymer is partially exposed to the environment and, in particular, can contact an environment that is a liquid or solid electrolyte (not shown) through the porous electrode 52. In this device, S is an ohmic contact to the semiconductor material 50, and P is an ohmic contact to the electrode 52.

In each instance, the electrical contact to the conducting polymer is labeled P. The primary considerations in selecting a particular contact geometry are the series resistance of the resulting device and the fraction of exposed polymer. The electrical contact to the semiconductor, labeled S, is generally made in a manner that assures a low resistance, nearly ohmic contact using techniques known to those skilled in the art.

Tunable Diodes

In a tunable diode, the semiconductor/exposed conducting polymer interface is placed in contact with an electrolyte to which a number of additional electrodes are contacted. An electrolyte is an ionic conductor including but not limited to liquid electrolytes such as aqueous sodium chloride or non-aqueous electrolytes such as tetramethyl ammonium tetrafluoroborate in acetonitrile, polymer electrolytes such as poly(propylene oxide)-sodium triflate polymer-salt complexes, and inorganic solid ionic conductors such as silver iodide or sodium beta-alumina. The primary considerations for choice of electrolyte are its physical properties, ionic conductivity, and chemical inertness over the range of electrochemical potential to be utilized. Furthermore, the electrolyte must not dissolve the conducting polymer or semiconductor to any appreciable extent.

One or more additional electrodes are contacted to the electrolyte. In particular, a counter electrode serves to provide a sink/source of electrons for the electrochemical oxidation or reduction of the conducting polymer. When desired, a reference electrode may be employed to provide a reference potential reading. The terms "counter electrode" and "reference electrode" are used as in conventional electrochemistry and are known to those skilled in the art. These electrodes may be as simple as a silver wire immersed in the electrolyte, such as a $AgNO_3$ solution or paste, or may be more complicated devices with diffusion barriers and multiple electroactive components. Counter and reference electrodes may be separate electrodes or may be a single dual-function electrode.

Figure 2A:
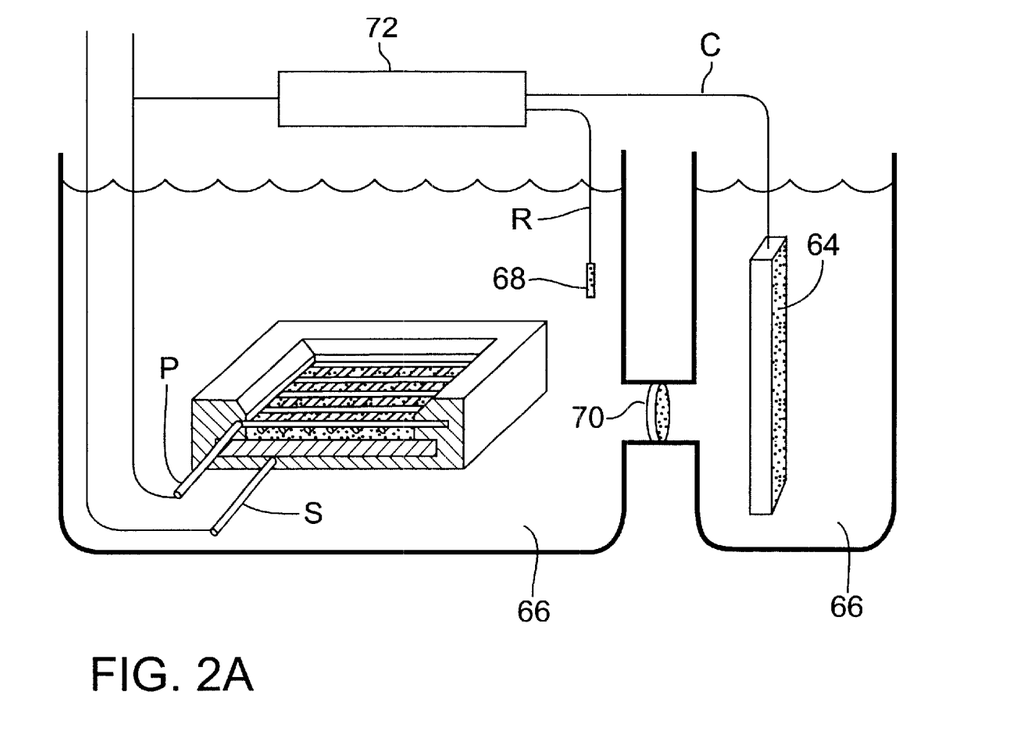
FIG. 2a shows a design utilizing a liquid electrolyte where the conducting polymer is made the working electrode of a traditional three electrode electrochemical cell.
Figure 2B:
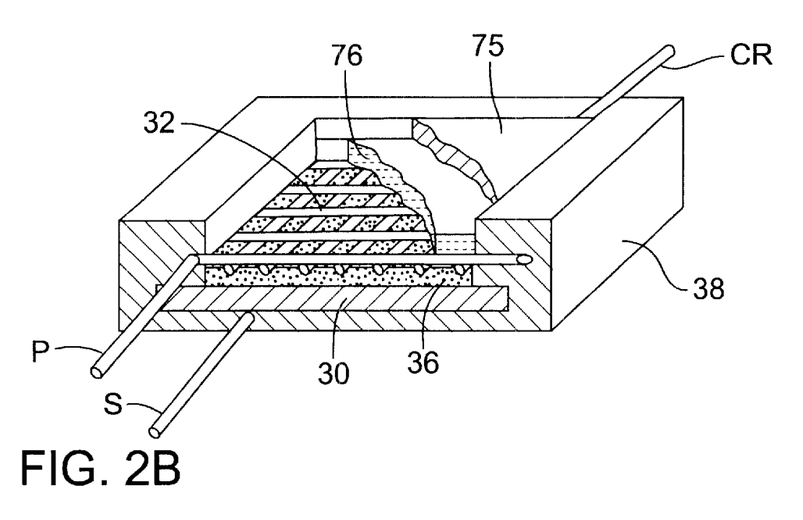
FIG. 2b shows an all solid state design where a solid electrolyte, such as a polymer electrolyte, is used in conjunction with a combined reference/counter electrode.

Two possible configurations of tunable diodes are shown. FIG. 2a shows conducting polymer being one electrode of a classic liquid electrochemical cell. FIG. 2b shows an all solid state version with the functions of the counter and reference electrodes combined into a single electrode. The major criteria in the choice of counter/reference electrode(s) are the charge capacity of the counter electrode and the electrochemical potential stability of the reference electrode. A referencing function to provide a stable electrochemical potential reading is only needed if one wishes to relate the diode characteristics to an external index. A stable reference potential is not required if the device is simply going to be driven until it has the desired characteristics.

More particularly, FIG. 2a shows a diode employing a device of the type shown in FIG. 1b in a classic liquid electrochemical cell. A Pt counter electrode 64 contacts a volume of electrolyte 66 at a distance away from the body of conducting polymer as does an Ag/Ag+ reference electrode 68. Two conductive leads are connected to the electrodes respectively: C is a contact to the counter electrode 64. R is a contact to the reference electrode 68. The electrolyte 66 is contained in two chambers separated by a porous membrane 70, such as a glass frit. The reference electrode 68 is located in the chamber that contains the semiconductor/exposed conducting polymer device. The counter electrode 64 is located in the other of the chambers. Because the counter electrode 64 and reference electrode 68 are separate, the operation of the device of FIG. 2a requires external electronics, herein termed a three-terminal potentiostat 72, capable of controlling the electrochemical potential of the polymer electrode vs. that of the reference electrode by passage of current between leads P and C.

A simpler, two-electrode configuration is shown in FIG. 2b. Configurations of the type shown in FIG. 2b can employ a device that is similar to the devices of FIGS. 1a–1c, except that the device includes an added assembly 75 that serves as a combination of a reference electrode, a counter electrode, and a separator. The particular device illustrated in FIG. 2b is derived from the device shown in FIG. 1b, with a reference/counter and separator assembly 75 extending across the opening 40 that is provided through the body of encapsulating material 38 such that electrolyte 76 is located between the assembly 75 and the polymer material 36 so that the polymer material 36 contacts the electrolyte 76. The reference/counter electrode assembly 75 can be constructed from a variety of materials. It is basically analogous to one electrode of rechargeable battery that provides a source/sink for electrons, and as much as possible, an electrochemical potential that is independent of charging level. The separator assembly is not always necessary depending on containment needs. Hence, the reference/counter electrode assembly could be constructed using techniques and materials known to those skilled in the art and in close parallel to rechargeable battery technology. A range of materials not currently used in rechargeable battery technology can also be used. For instance, assembly 75 could consist of a layer of a mixed valent ruthenium coordination complex with poly(4-vinylpyridine). To assure constant electrochemical potential, the amount of material would have to be such that its charge capacity exceeded the useful charge capacity of the conducting polymer layer so that the mixed valency ratio of the coordination polymer, and hence its electrochemical potential, remained constant during device operation. A conductive lead CR is electrically connected the reference/counter and separator assembly 75. A control device, such as a two terminal power supply (not shown) electrically connected to the body of conducting polymer and to the electrode, is used to control the potential of the polymer electrode (P vs. CR). Application of a control voltage across P—CR induces a current until the electrochemical potential of the conjugated polymer 36 vs. CR matches the applied control voltage. The device of FIG. 2b can be constructed so that the electrolyte is contained in a chamber defined by a surrounding wall, with the illustrated wall comprising portions of the body 36 of a conducting polymer, the grid electrode 32, the body 38 of insulating material, and the combination electrode 75.

In the embodiments of both FIGS. 2a and 2b, the electrical current flowing to/from lead P acts to oxidize or reduce the conducting polymer with concomitant reduction/ oxidation at the counter electrode. The electrolyte serves to complete the circuit. For the remainder of this detailed description of tunable diodes, setting the electrochemical potential of the polymer electrode vs. the reference electrode is discussed with an understanding that somewhat different external electronics are involved and that current may be either flowing to a separate counter electrode or a combined reference/counter electrode. And, in the remainder of this detailed description of tunable diodes, references to a lead R should be read to refer also to the lead CR for those configurations that employ a combined reference/counter electrode.

The device operates as a diode with tunable electrical characteristics. The device is used to manipulate an electrical signal applied across the polymer/semiconductor (P-S) contact. Diode characteristics are known to those skilled in the art and generally include, but are not limited to, current rectification and an exponential dependence of current on applied potential for one sign of the applied bias (as described for instance by equation (1)), and a voltage dependent differential capacitance. The precise action of the device on the electrical signal applied to the P-S contact can be manipulated with the application of a control voltage across the polymer-reference (P-R) contact. The selected P-R control voltage is applied for sometime (need not be continuously) to drive the oxidation or reduction of the conducting polymer until its electrochemical potential is given by the applied P-R control voltage. The P-R control voltage alters the electrical characteristics of the P-S interface primarily, although not exclusively, by altering its Schottky barrier height. The Schottky barrier height is a central parameter known to those skilled in the art and is a measure of the equilibrium interfacial potential barrier. A wide range of electrical properties depend on the Schottky barrier height. For instance, the current-voltage behavior of the P-S interface depend on the Schottky barrier height as described by equations (1) and (2). Hence, the current-voltage behavior of the tunable diode can be described by equations (1) and (2) with a continuously variable $\phi_b$ that is set by the P-R control voltage. In essence, the tunable diode allows one to control the central defining parameter of a diode in a single device much as a potentiometer allows one to control the central defining parameter of a resistor, its resistance.

Considering the tunable diode as a three terminal (P, S, R) device, the operation of the tunable diode provides a new type of electronic circuit element: a variable-barrier diode. The ability to control the current voltage characteristics across two terminals of a three terminal device by a voltage signal across another pair of terminals (one in common) is reminiscent of transistor operation. Unlike a transistor, the device described herein is a voltage-controlled device and hence bears stronger operational similarity to vacuum tube devices such as the vacuum tube triode. The electrical characteristics can also be permanently and reversibly switched providing for potential application in information storage.

A significant feature of the present device is the architecture, which leaves the conducting polymer exposed for subsequent electrochemical or chemical manipulation. A key to the success of this approach is the use of a polymer that is tunable over a wide range of electrochemical potentials while still maintaining good conductivity. This is a unique property of many conducting polymers in particular conjugated organic polymers and can be expanding upon by using blends of conducting polymers. Furthermore, the ability for ions to diffuse through the polymer structure allows for the electrochemical potential to be manipulated in an operating device—a feature that cannot be achieved with traditional inorganic diodes. A second key is the use of materials with appropriate energetics and chemical reactivities such that the barrier height of the semiconductor—conducting polymer interface is sensitive to changes in the electrochemical potential of the conducting polymer. In particular, the macromolecular structure implies the absence of surface dangling bonds thereby minimizing the potential for deleterious interfacial reactions.

EXAMPLE 1

This example describes a tunable diode, generally of the type shown in FIGS. 1b and 2a, fabricated from n-type indium phosphide (n-InP) and poly(pyrrole). The specific procedures used to fabricate this tunable diode as well as measurement details are given below:

Fabrication

This embodiment of the tunable diode consisted of an n-InP | poly(pyrrole) | gold minigrid sandwich (analogous to FIG. 1b). To fabricate it, a piece of single crystal n-InP (100, $N_D \approx 1 \times 10^{16}$ cm$^{-3}$, 350 µm thick, Crystacomm, Inc.), ohmically back contacted with Ga/In eutectic, was first imbedded ≈50 µm below the flat surface of an epoxy encasement. A gold minigrid (60 µm wire diameter, 250 µm spacing, 65% open, Goodfellow Inc.) was then suspended above the n-InP with its edges ohmically contacted and embedded in epoxy. The n-InP electrode was doubly etched (30s 0.05% Br$_2$/MeOH, MeOH rinse, 30s 30% NH4OOH$_{(aq)}$, water rinse) and immediately transferred to a dry N$_2$ environment. All subsequent manipulations were carried out under dry N$_2$. Poly(pyrrole) with an as-synthesized conductivity of 10–20$\Omega^{-1}$ cm$^{-1}$ was deposited from solution through the gold grid using the method of Freund et al. (M .S. Freund et al., Curr. Sep. 13, 66 (1994)) to a thickness sufficient to span the gold grid and the n-InP. The resulting structure was placed into an electrochemical cell filled with 0.1 M tetrabutylammonium tetrafluoroborate (Bu$_4$NBF$_4$, dried for a minimum of 7 days in vacuo at 80° C., Johnson Matthey) in acetonitrile (CH$_3$CN, distilled under: N$_2$ from CaH$_2$ then P$_2$O$_5$, Mallinckrodt). The electrochemical cell was fitted with a non-aqueous Ag/AgNO$_3$ (≈0.005 M in 0.10 M Bu$_4$NBF$_4$/CH$_3$CN) reference electrode and a Pt counter electrode separated off with a porous glass frit.

Measurement Techniques

The electrochemical potential of the poly(pyrrole) vs. the reference electrode, $E_{pp}$, was controlled using a Solartron 1287 potentiostat/galvanostat and the gold grid contact. The same instrument was used for current-voltage measurements across the n-InP | poly(pyrrole) interface. $E_{pp}$ was appropriately converted and is reported relative to aqueous SCE.

Characterization

Figure 3:
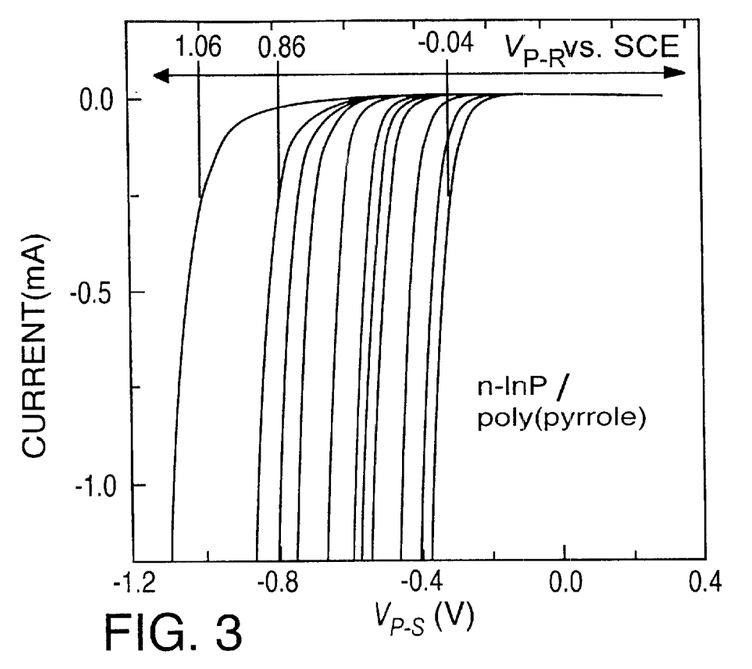
FIG. 3 is a chart showing graphs of current vs. voltage behavior of a tunable diode based on n-InP and poly (pyrrole). The current-voltage behavior of the n-InP–poly (pyrrole) interface is shown as a function of the electrochemical potential of the poly(pyrrole), which is set by the control voltage $V_{P-R}$. The far right trace is for $V_{P-R}=0.04V$ vs. SCE with the next nine traces to its left a result of incremental 0.1V positive shifts in $V_{P-R}$ up to 0.86V vs. SCE. The far left trace is for $V_{P-R}=1.06V$ vs. SCE. The abscissa is the voltage applied across the n-InP | poly (pyrrole) contact, and the resulting current is the ordinate. Negative applied potentials correspond to higher electron energy in the n-InP relative to the poly(pyrrole), and negative currents correspond to net electron flow from the n-InP to the poly(pyrrole).

This embodiment of the tunable diode demonstrates the use of an oxidatively doped conjugated polymer as the conducting polymer element. It demonstrates the central principle of the tunable diode and shows the level of control that can be achieved. The example focuses on how the current-voltage behavior of the P-S interface can be manipulated by a control voltage across P-R that is used to set the electrochemical potential of the poly(pyrrole), $E_{pp}$. FIG. 3 shows a family of current-voltage curves collected for an n-InP/poly(pyrrole) tunable diode. Each curve represents the current-voltage characteristics across P-S for a specific value of $E_{pp}$ (set by a control voltage applied across P-R for some time). Each curve exhibits the rectification behavior characteristic of a classic diode and well modeled by equation (1) with n=1.4 over the majority of electrochemical potentials.

Figure 4:
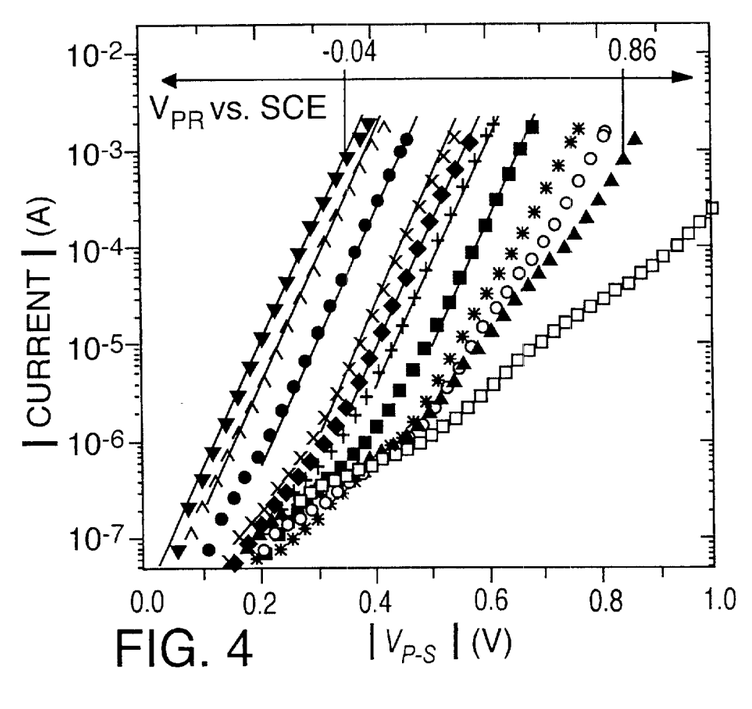
FIG. 4 is a chart showing graphs, in semilogarithmic representation, of the data in FIG. 3.

In FIG. 3, forward bias corresponds to negative voltage applied to S relative to P. FIG. 4 shows a semilogarithmic representation of this data showing the characteristic exponential dependence of current on voltage in forward bias. The central demonstration of the example is the ability to shift the current-voltage traces across the applied voltage axis by manipulating $E_{pp}$. Over the range of $E_{pp}$ shown in FIG. 3, such shifts can be effected continuously and reversibly, with an increase in the level of polymer oxidation (positive shift in $E_{pp}$) resulting in an increase in the magnitude of the forward bias potential required to pass a particular current, termed $|V_F|$. At $I_F=1$ mA, $|V_F|$ is observed to shift by over 0.6V in response to a 1.1V change in $E_{pp}$. The increase in $|V_F|$ with $E_{pp}$ is linear with $d|V_F|/dE_{pp}=0.61\pm0.04$. Considering more extreme values of $E_{pp}$ than shown in FIG. 3: the system becomes irreversible for $E_{pp}>1.1$V vs. SCE, presumably due to over oxidation of the polymer and reaction with electrolyte impurities; rectifying behavior is lost for $E_{pp}$ somewhat more negative than the formal reduction potential of poly(pyrrole) ($E^{0/+}_{pp}=-0.1$V vs. SCE (14)) due to reduction of the polymer to its insulating state.

A figure of merit for semiconductor interfaces is the index of interface behavior, S. This quantitatively describes the variation of $\phi_b$ with the electrochemical potential of the semiconductor contact ($S=d\phi_b/dE_c$ where $E_c$ is the electrochemical potential of the material contacting the semiconductor). A larger value of S indicates greater control over the junction properties with the ideal value of S=1 being the theoretical maximum. For the n-InP/poly(pyrrole) tunable diode in this example, $S\approx0.5$. Although substantially less than the ideal value of S=1, this value is still much better than observed at n-InP | metal contacts. Newman et al. measured $\phi_b$ for a series of n-InP | metal Schottky junctions and found the $\phi_b$ values to be pinned over a narrow 0.22V range for 9 metals covering a 1.05 eV range in electrochemical potential (work function ($\phi_m$)) In terms of operational characteristics, this implies that $|V_F|$ can only be varied by 0.22V, whereas at the n-InP | poly(pyrrole) interface can be varied by over 0.6V for a similar change in electrochemical potential. Furthermore, little correlation was observed between $\phi_b$ and $\phi_m$ at the n-InP | metal interface. A linear regression of $\phi_b$ vs. $\phi_m$ using the data of Newman et al. yielded a correlation coefficient of R=0.1 and S=0.02. In contrast, excellent correlation between $|V_F|$ and $E_{pp}$ are observed at the n-InP | poly(pyrrole) interface with S=0.5 as mentioned earlier and R=0.98.

EXAMPLE 2

Figure 5:
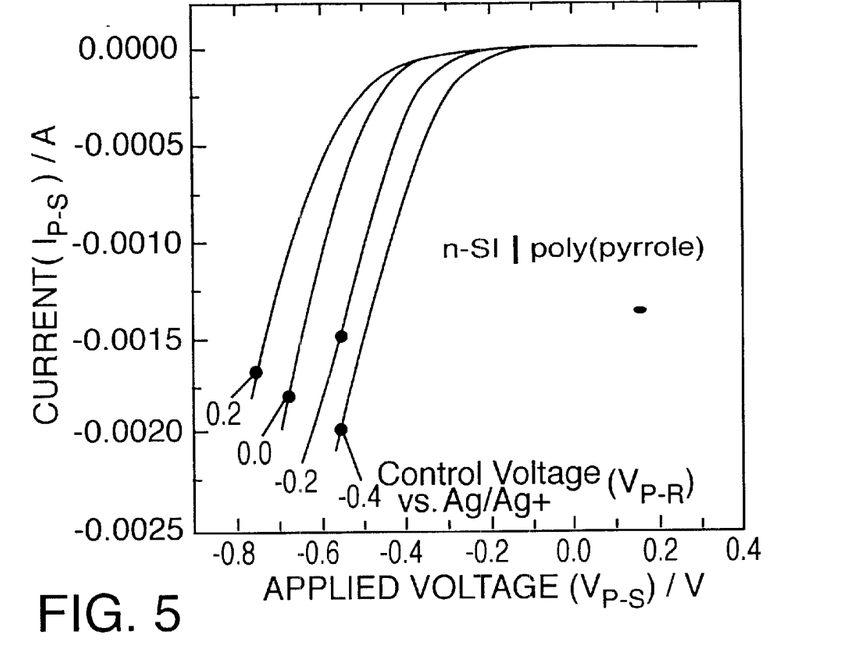
FIG. 5 is a chart showing graphs of current vs. voltage behavior of a tunable diode based on n-Si and poly(pyrrole). Sign conventions and definitions are as in FIG. 3.

This example demonstrates the generality of the tunable diode concept in terms of the choice of semiconductor. Characterization of a n-type silicon (n-Si)/polypyrrole interface is shown. Fabrication and measurement procedures were similar to that of Example 1. The etching procedure for silicon was somewhat different than for n-InP consisting of two treatments of 30s 48%HF, 30s $H_2O$ rinse. A family of current voltage curves for this embodiment of the tunable diode is shown in FIG. 5. This figure is qualitatively similar to the tunable diode of Example 1.

EXAMPLE 3

Figure 6:
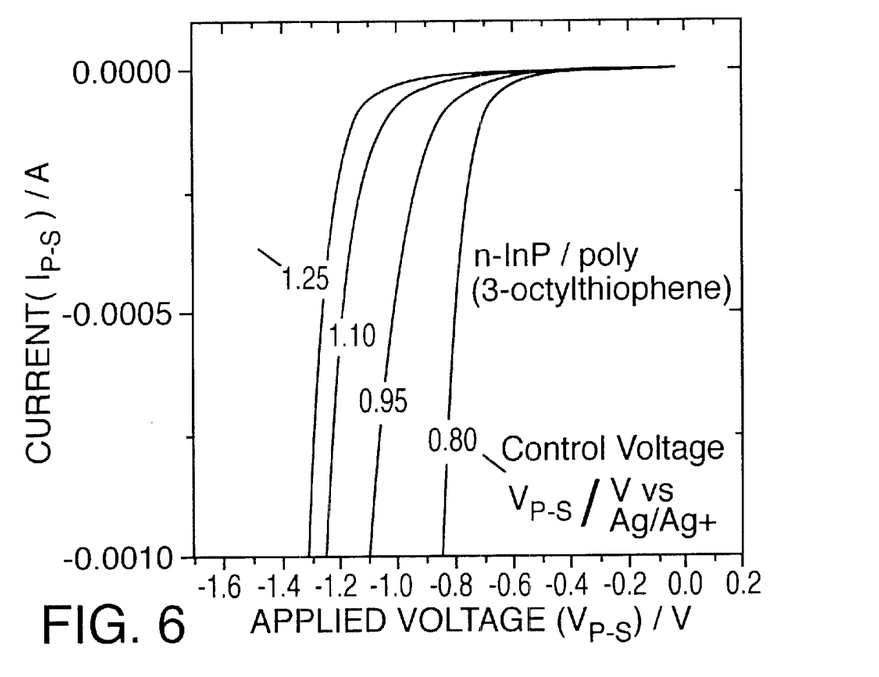
FIG. 6 is a chart showing graphs of current vs. voltage behavior of a tunable diode based on n-InP and poly(3-octylthiophene). Sign conventions and definitions are as in FIG. 3.

This example demonstrates the generality of the tunable diode concept in terms of the choice of conducting polymer. Characterization of an n-type InP/poly(3-octylthiophene) interface is shown. Fabrication and measurement procedures were similar to that of Example 1. Poly(3-octylthiophene) was synthesized by known literature methods and cast from solution. A family of current voltage curves for this embodiment of the tunable diode is shown in FIG. 6. This figure is qualitatively similar to the tunable diode of Example 1.

EXAMPLE 4

Figure 7:
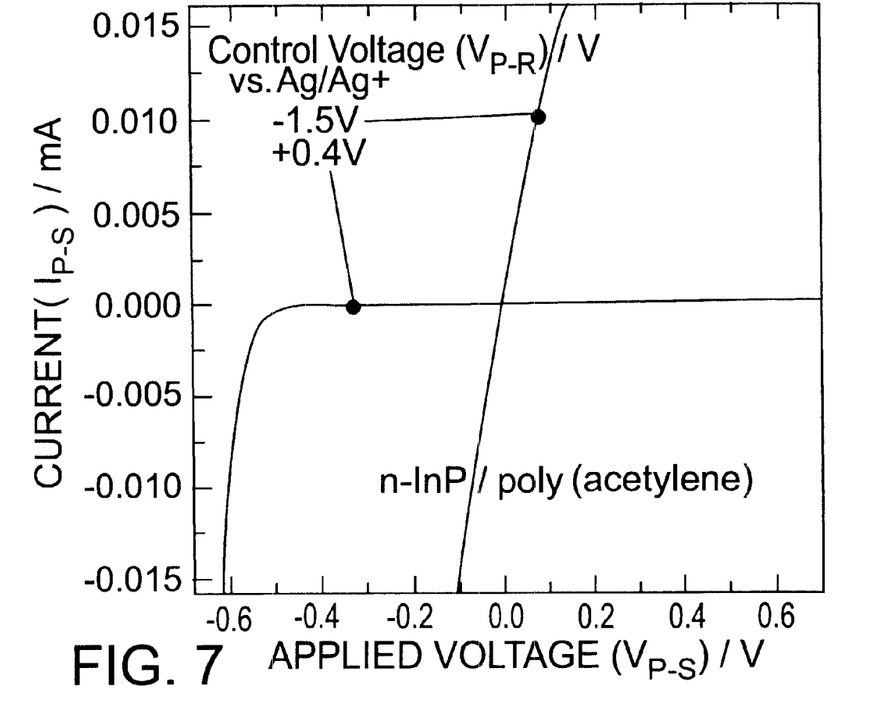
FIG. 7 is a chart showing graphs of current vs. voltage behavior of a tunable diode based on n-InP and poly (acetylene). Sign conventions and definitions are as in FIG. 3.

This example demonstrates the generality of the tunable diode to conducting polymers that can be both oxidatively doped so as to carry a net positive charge on the polymer backbone and reductively doped so as to carry a net negative charge on the polymer backbone. All of the examples shown above utilized a conducting polymer that was oxidatively doped with the differing electrochemical potentials corresponding to differing degrees of net oxidation. Certain conducting polymers, such as poly(acetylene), can be both oxidatively and reductively doped. This opens the possibility for a very large variation in electrochemical potential. For poly(acetylene) the conductivity windows for the net oxidized and net reduced forms are separated by over 1.5 eV. In this example, the characterization of a n-InP/poly (acetylene) tunable diode is shown. Fabrication and measurement procedures were similar to that of Example 1. Poly(acetylene) was directly polymerized on the surface of the n-InP via the ring-opening metathesis polymerization of cyclooctatetraene as reported in the literature. FIG. 7 shows the current-voltage curves for two electrochemical potentials of the poly(acetylene). The electrochemical potential of the reductively doped polymer (=$-1.5$V vs. Ag/Ag+) is so negative that the resulting Schottky barrier sufficiently low that the interface behaves essentially like an ohmic contact over the current range shown. This demonstrates the ability of the tunable diode to essentially be switched between a current rectifier and a resistor.

Fabricated Diodes with Specific Electrical Characteristics

The operational principle upon which the tunable diodes described above are based also provides a means to fabricate diodes with fixed but tailored electrical characteristics. It is the first general approach to continuously and precisely controlling the electrical characteristics of Schottky-type semiconductor diodes. In particular, it provides a means to fabricate diodes with Schottky barrier heights that vary continuously in a predictable manner over a range of greater than 0.5 eV.

To fabricate a diode with specific electrical characteristics, one first fabricates a semiconductor/ conducting polymer interface. One of two approaches can then be taken. The first approach involves a chemical treatment step and does not necessarily require that the polymer electrical contact leave the polymer partially exposed. The polymer electrical contact can completely cover the conducting polymer if it is made following the chemical treatment step. The chemical treatment involves reaction of the deposited polymer film with a chemical reagent to set the electrochemical potential of the conducting polymer. The chemical reagent consists of an oxidant or reductant with a well defined electrochemical potential such as but not limited to solutions containing: ferrocene$^{+/0}$, decamethylferrocene$^{+/0}$ methylviologen $^{2+/+/0}$, N,N,N',N'-tetramethylphenylenediammine$^{2+/+/0}$. The polymer is allowed to equilibrate with the chemical reagent thereby setting its electrochemical potential and hence the characteristics of the diode. After chemical treatment, which may also include a rinsing step, the diode is packaged as necessary to preserve the electrochemical potential of the polymer.

The second approach, which offers greater flexibility, requires the electrical contact to the conducting polymer leave the polymer partially exposed. As with the tunable diode, the polymer is placed in contact with an electrolyte to which one or 30 more electrodes (C and R or C/R) are also contacted. The electrochemical potential of the conjugated polymer is then set electrochemically as described above for the tunable diode. For example, a voltage is applied across an electrode and an electrical contact to the body of conducting polymer in an amount sufficient to set the electrochemical potential of the conducting polymer at a desired level. The diode is then removed from contact with the electrolyte, rinsed if necessary, and packaged in a manner to preserve the set electrochemical potential and hence the set electrical characteristics.

Chemical Sensors

As the electrical characteristics of the semiconductor/conducting polymer interface depend on the electrochemical potential of the conducting polymer, the tunable diode platform can serve as a general electrochemical transducer or probe for a wide range of potentiometric sensing schemes. As an electrochemical transducer, all that is needed is the semiconductor/exposed conducting polymer interface in a geometry such as those depicted in FIGS. 1a–1c, wherein at least a portion of the body conducting polymer is open for exposure to the environment. Electrolyte and the additional counter and reference electrodes are not required as in the tunable diode. The exposed polymer of the probe is placed in contact with an environment to be sensed. This contact can either be direct or through a mediating layer that serves to provide selectivity. The polymer is allowed to electrochemically equilibrate with its environment and its electrochemical potential is then determined by a metering device that measures one or more electrical characteristics of the semiconductor/conducting polymer interface, most usefully characteristics that are indicative of Schottky barrier height. Electrical characteristics that can be measured include Schottky barrier height, current in response to a particular applied voltage, applied voltage required to pass a particular current, and capacitance.

A particular advantage of this means of potentiometric detection is that only a single electrode consisting of the semiconductor/conducting polymer interface is required. An additional reference electrode is not required.

EXAMPLE 5

Figure 8:
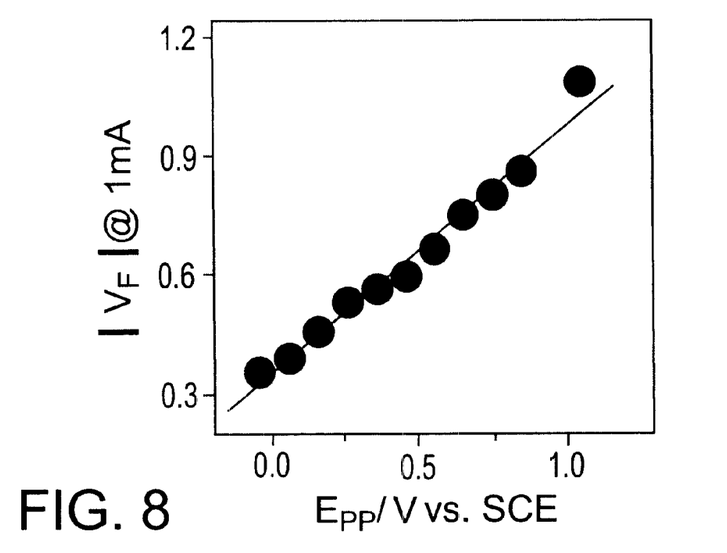
FIG. 8 is a chart showing a graph of forward bias potential required to pass 1 mA of current vs. electrochemical potential for a semiconductor/exposed conducting conjugated polymer interface as an electrochemical transducer. The specific system is n-InP/poly(pyrrole). The observed dependence implies that the electrical characteristics of the n-InP/poly(pyrrole) interface determine the electrochemical potential of the conjugated polymer.

This example serves to show the utility of the tunable diode as an electrochemical transducer that can serve as a platform for a wide range of potentiometric sensing modalities. This example uses the n-InP/poly(pyrrole) interface as fabricated in Example 1. The potential, termed $V_F$, required to pass 1 mA of current across P-S (i.e. across the InP/poly(pyrrole) interface) was observed as the electrochemical potential of the poly(pyrrole), $E_{pp}$, changed. FIG. 8 shows the result of this experiment. The near linear relationship between $V_F$ and $E_{pp}$ implies that $V_F$ can be used as a sensor of electrochemical potential. Note that this measurement of electrochemical potential did not require the use of a reference electrode. It relies only on the characteristics of the conducting polymer/inorganic semiconductor interface. Many other observables besides $V_F$ can be used in a similar manner to sense electrochemical potential such as but not limited to, the current in response to a constant applied voltage across P-S and the capacitance of the P-S interface.

EXAMPLE 6

Figure 9:
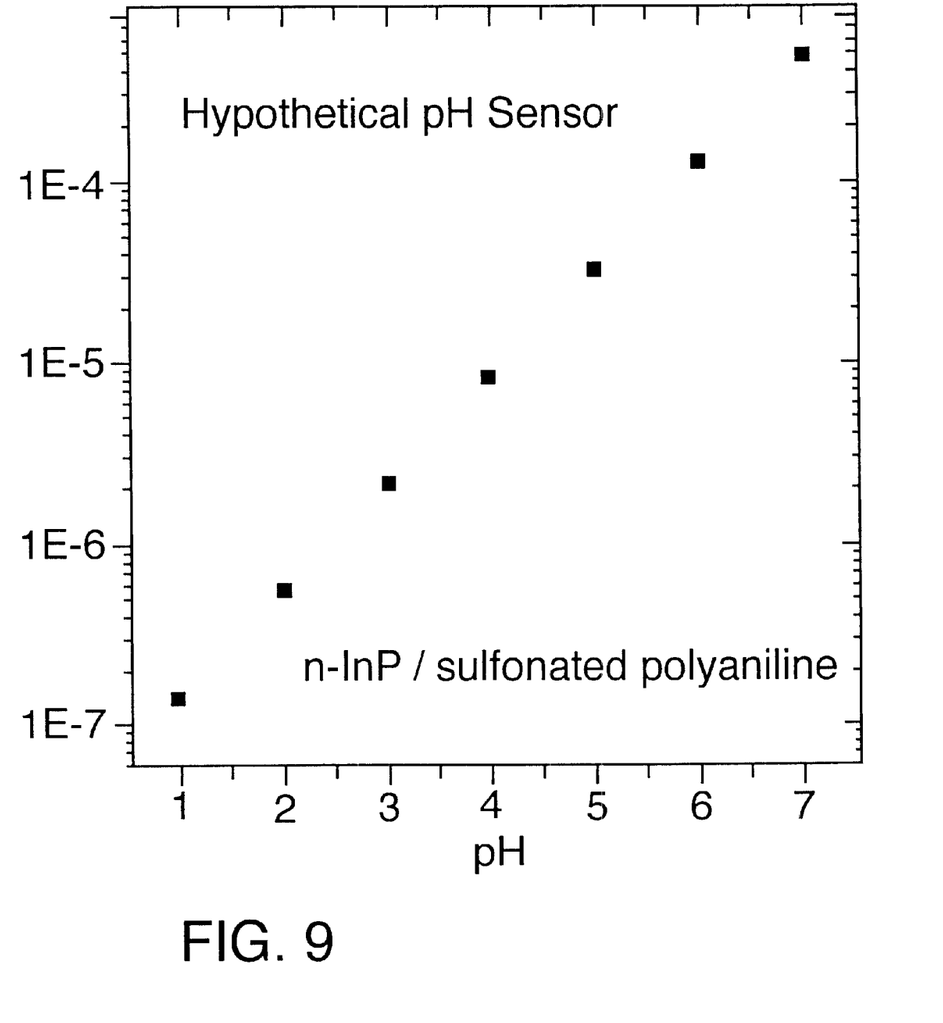
FIG. 9 is a chart showing a graph of current across a polymer-semiconductor interface vs. pH for a hypothetical pH sensor using a n-InP/exposed polyaniline interface. The current of the device changes orders of magnitude in response to pH.

This hypothetical example demonstrates how the tunable diode construct can be used as a pH sensor. In order to do so, one utilizes a conducting polymer whose electrochemical potential depends on pH. Polyaniline and its derivatives are such polymers. For instance, sulfonated polyaniline exhibits a dependence of electrochemical pH on the order of 70 mV/pH (E. Karyakina et al., Anal. Lett. 27, 25 2871 (1994)). FIG. 9 shows the hypothetical response of an n-InP/sulfonated polyaniline sensor. The sensor would be constructed as in FIG. 1b where the conducting polymer layer is sulfonated polyaniline. The figure shows the current across the n-InP/polyaniline layer for an applied potential, $V_{ps}$, of 0.1V as a function of pH. The hypothetical curve was constructed using equations (1) & (2) assuming the electrochemical potential of sulfonated polyaniline varies 70 mV per unit pH and that barrier height varies 0.5 units for each 1 unit change in electrochemical potential.

Having illustrated and described the principles of the invention in the preferred embodiments, it should be apparent to those skilled in the art that the invention can be modified in arrangement and detail without departing from such principles. Accordingly, I claim all modifications coming within the spirit and scope of the following claims:

I claim:

1. A microelectronic device comprising:
    a body of conducting polymer;
    an electrical contact to the body of conducting polymer;
    a body of semiconductor material in electrical contact with the body of conducting polymer; and
    an electrical contact to the body of semiconductor material, the device being configured such that at least a portion of the body of conducting polymer is exposed to the environment.

2. The device of claim 1 wherein:
    at least a portion of the body of conducting polymer is exposed to an environment that is an electrolyte; and
    the device further comprises at least one electrode that is in contact with the electrolyte at a distance away from the body of conducting polymer.

3. The device of claim 1 further comprising:
    an insulating substrate, the body of semiconductor material being supported on the substrate; and
    a electrically conductive contact supported on the substrate at a distance from the body of semiconductor material, the body of conducting polymer being positioned in physical contact with both the body of semiconductor material and the electrically conductive contact such that an electrical connection exists between the body of semiconductor material and the electrically conductive contact via the conducting polymer.

4. The device of claim 1 further comprising:
    an insulating substrate, the body of semiconductor material being supported on the substrate and the body of conducting polymer being superposed on and in physical contact with the body of semiconductor material; and
    a grid electrode superposed on and in physical contact with the body of conducting polymer, the grid being sufficiently porous that at least a portion of the body of conducting polymer is exposed to the environment via openings through the grid electrode.

5. The device of claim 1 further comprising:
    an insulating substrate, the body of semiconductor material being supported on the substrate and the body of conducting polymer being superposed on and in physical contact with the body of semiconductor material; and a porous electrically conductive contact superposed on and in physical contact with the body of conducting polymer, the electrically conductive contact being sufficiently porous that at least a portion of the body of conducting polymer is exposed to the environment via openings through the porous electrically conductive contact.

6. The device of claim 1 wherein the body of semiconductor material is at least partially encapsulated so that the body of semiconductor material is not exposed to the environment.

7. A diode comprising:

an electrolyte;

a body of conducting polymer, at least a portion of the body of conducting polymer being in contact with the electrolyte;

a body of semiconductor material in electrical contact with the body of conducting polymer material; and at least one electrode that is in contact with the electrolyte at a distance away from the body of conducting polymer.

8. The diode of claim 7 further comprising a control device electrically connected to the body of conducting polymer and to the electrode to control the electrochemical potential of the polymer.

9. The diode of claim 8 wherein:

the electrode comprises at least two separate electrodes that are in contact with the electrolyte at a distance away from the body of conducting polymer; and the control device is a potentiostat.

10. The diode of claim 7 wherein:

the electrode is a single combination electrode that serves as both a reference electrode and a counter electrode.

11. The diode of claim 10 wherein:

the electrolyte is contained in a chamber defined by a wall; and the combination electrode serves as at least a portion of the wall the that defines the chamber.

* * * * *